(12) United States Patent
Nesper et al.

(10) Patent No.: US 8,382,048 B2
(45) Date of Patent: Feb. 26, 2013

(54) SURGICAL HOLDING ARM AND SURGICAL HOLDING DEVICE

(75) Inventors: Markus Nesper, Tuttlingen (DE); Dieter Weisshaupt, Immendingen (DE); Matthias Wand, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 282 days.

(21) Appl. No.: 12/661,181

(22) Filed: Mar. 10, 2010

(65) Prior Publication Data
US 2010/0243840 A1 Sep. 30, 2010

(30) Foreign Application Priority Data
Mar. 20, 2009 (DE) .......................... 10 2009 015 391

(51) Int. Cl.
*F16M 13/00* (2006.01)

(52) U.S. Cl. ...................... 248/160; 248/274.1; 600/206; 600/229

(58) Field of Classification Search .................. 248/104, 248/160, 274.1; 600/206, 228, 229
See application file for complete search history.

(56) References Cited

U.S. PATENT DOCUMENTS

| | | | | |
|---|---|---|---|---|
| 2,510,198 A * | 6/1950 | Tesmer | ..................... | 248/229.25 |
| 3,168,274 A * | 2/1965 | Street | ........................... | 248/176.3 |
| 3,529,797 A * | 9/1970 | Street | ............................ | 248/160 |
| 4,949,927 A * | 8/1990 | Madocks et al. | ........... | 248/276.1 |
| 5,348,259 A * | 9/1994 | Blanco et al. | ............. | 248/276.1 |
| 5,513,827 A * | 5/1996 | Michelson | ................. | 248/279.1 |
| 5,662,300 A | 9/1997 | Michelson | | |
| 5,865,730 A | 2/1999 | Fox et al. | | |
| 5,899,425 A | 5/1999 | Corey Jr. et al. | | |
| 5,984,864 A | 11/1999 | Fox et al. | | |
| 5,993,464 A | 11/1999 | Knodel | | |
| 6,013,027 A | 1/2000 | Khan et al. | | |
| 6,066,144 A | 5/2000 | Wolf et al. | | |
| 6,210,325 B1 * | 4/2001 | Bartie et al. | .................. | 600/229 |
| 6,345,793 B1 * | 2/2002 | Mauro | ......................... | 248/160 |
| 6,520,495 B1 * | 2/2003 | La Mendola | .................... | 269/45 |
| 6,581,889 B2 * | 6/2003 | Carpenter et al. | ............ | 248/160 |
| 6,663,563 B1 * | 12/2003 | Sharratt | ........................ | 600/228 |
| 6,698,044 B2 * | 3/2004 | Greenfield et al. | ............... | 5/624 |
| 6,983,930 B1 * | 1/2006 | La Mendola et al. | ........... | 269/45 |
| 7,136,280 B2 * | 11/2006 | Jobs et al. | ................. | 361/679.06 |
| 7,182,731 B2 * | 2/2007 | Nguyen et al. | ................ | 600/229 |
| 7,730,565 B1 * | 6/2010 | Masson | ............................. | 5/646 |
| 2006/0094933 A1 * | 5/2006 | Goldfarb et al. | .............. | 600/229 |

FOREIGN PATENT DOCUMENTS

| | | |
|---|---|---|
| DE | 298 01 807 | 6/1998 |
| DE | 203 18 312 | 2/2004 |
| DE | 103 34 135 | 3/2005 |
| DE | 698 36 575 | 9/2007 |

* cited by examiner

*Primary Examiner* — Bradley Duckworth
(74) *Attorney, Agent, or Firm* — Lipsitz & McAllister, LLC

(57) ABSTRACT

A surgical holding arm has a plurality of holding arm members which are coupled to one another and a tensioning device for tensioning the holding arm members against one another. The tensioning device is designed in such a manner that the holding arm can be brought from an operative position, in which the holding arm members are tensioned against one another so as to be immovable, into an adjusting position, in which the holding arm members can be moved relative to one another. The holding arm can be brought, in addition, into a cleaning position, in which adjacent holding arm members can be moved away from one another further than in the adjusting position.
Furthermore, a surgical holding device is described.

24 Claims, 13 Drawing Sheets

SURGICAL HOLDING ARM AND SURGICAL HOLDING DEVICE

CROSS-REFERENCE TO RELATED APPLICATIONS

This application claims the benefit of German Patent Application No. 10 2009 015 391.8 filed on Mar. 20, 2009.

The present disclosure relates to the subject matter disclosed in German application number 10 2009 015 391.8 of Mar. 20, 2009, which is incorporated herein by reference in its entirety and for all purposes.

FIELD OF THE INVENTION

The present invention relates to surgical holding arms generally, and more specifically to a surgical holding arm with a plurality of holding arm members which are coupled to one another and a tensioning device for tensioning the holding arm members against one another, wherein the tensioning device is designed in such a manner that the holding arm can be brought from an operative position, in which the holding arm members are tensioned against one another so as to be immovable, into an adjusting position, in which the holding arm members are movable relative to one another.

In addition, the present invention relates to surgical holding devices for holding and securing surgical instruments and/or surgical tools and/or surgical equipment generally, and more specifically to a surgical holding device for holding and securing surgical instruments and/or surgical tools and/or surgical equipment, comprising at least one holding arm with a plurality of holding arm members which are coupled to one another and a tensioning device for tensioning the holding arm members against one another, wherein the tensioning device is designed in such a manner that the holding arm can be brought from an operative position, in which the holding arm members are tensioned against one another so as to be immovable, into an adjusting position, in which the holding arm members are movable relative to one another.

BACKGROUND OF THE INVENTION

Surgical holding arms and holding devices of the type described at the outset are normally used during surgical procedures for the purpose of holding, in particular, instruments, tools or equipment of a medical and surgical type so that a person assisting a surgeon or the operating surgeon do not have to hold the respective devices themselves. As a result of the design of the holding arm in the manner described, this can be brought into a desired shape in a simple manner in the adjusting position and fixed in the predetermined shape by transferring the tensioning device from the adjusting position into the operative position. The holding arm which is essentially flexible in the adjusting position is, consequently, adequately rigid in the operative position for holding the instruments, tools or equipment securely and permanently in the position required for a surgical or medical procedure.

Surgical holding arms of the type described at the outset can, in particular, become soiled during the course of a surgical procedure. They will, therefore, be cleaned and sterilized prior to any further use.

Therefore, it would be desirable have a surgical holding arm as well as a surgical holding device of the type described at the outset which can be cleaned more easily and better.

SUMMARY OF THE INVENTION

In a first aspect of the invention, a surgical holding arm has a plurality of holding arm members coupled to one another and a tensioning device for tensioning the holding arm members against one another. The tensioning device is designed in such a manner that the holding arm is adapted to be brought from an operative position, the holding arm members being tensioned against one another so as to be immovable in said operative position, into an adjusting position, the holding arm members being movable relative to one another in said adjusting position. The holding arm is adapted, in addition, to be brought into a cleaning position, adjacent holding arm members being movable away from one another further in said cleaning position than in the adjusting position.

In a second aspect of the invention, a surgical holding device for holding and securing surgical instruments and/or surgical tools and/or surgical equipment, comprises at least one holding arm with a plurality of holding arm members coupled to one another and a tensioning device for tensioning the holding arm members against one another. The tensioning device is designed in such a manner that the holding arm is adapted to be brought from an operative position, the holding arm members being tensioned against one another so as to be immovable in said operative position, into an adjusting position, the holding arm members being moveable relative to one another in said adjusting position. The holding arm is, in addition, adapted to be brought into a cleaning position, adjacent holding arm members being movable away from one another further in said cleaning position than in the adjusting position.

BRIEF DESCRIPTION OF THE DRAWINGS

The foregoing summary and the following description may be better understood in conjunction with the drawing figures, of which.

DETAILED DESCRIPTION OF PREFERRED EMBODIMENTS OF THE INVENTION

Figure 1:
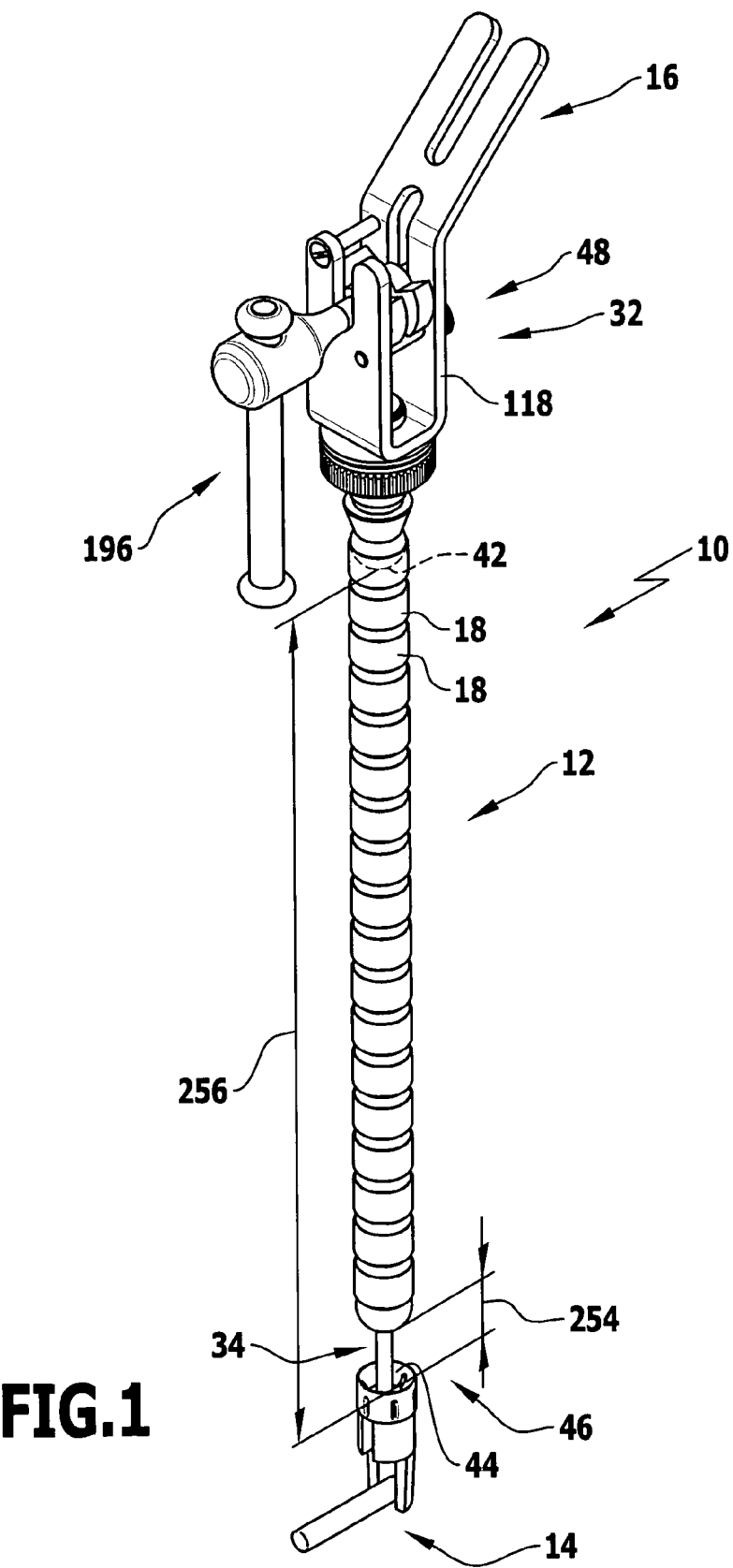
FIG. 1: shows a perspective overall view of a surgical holding arm in the cleaning position.
Figure 2:
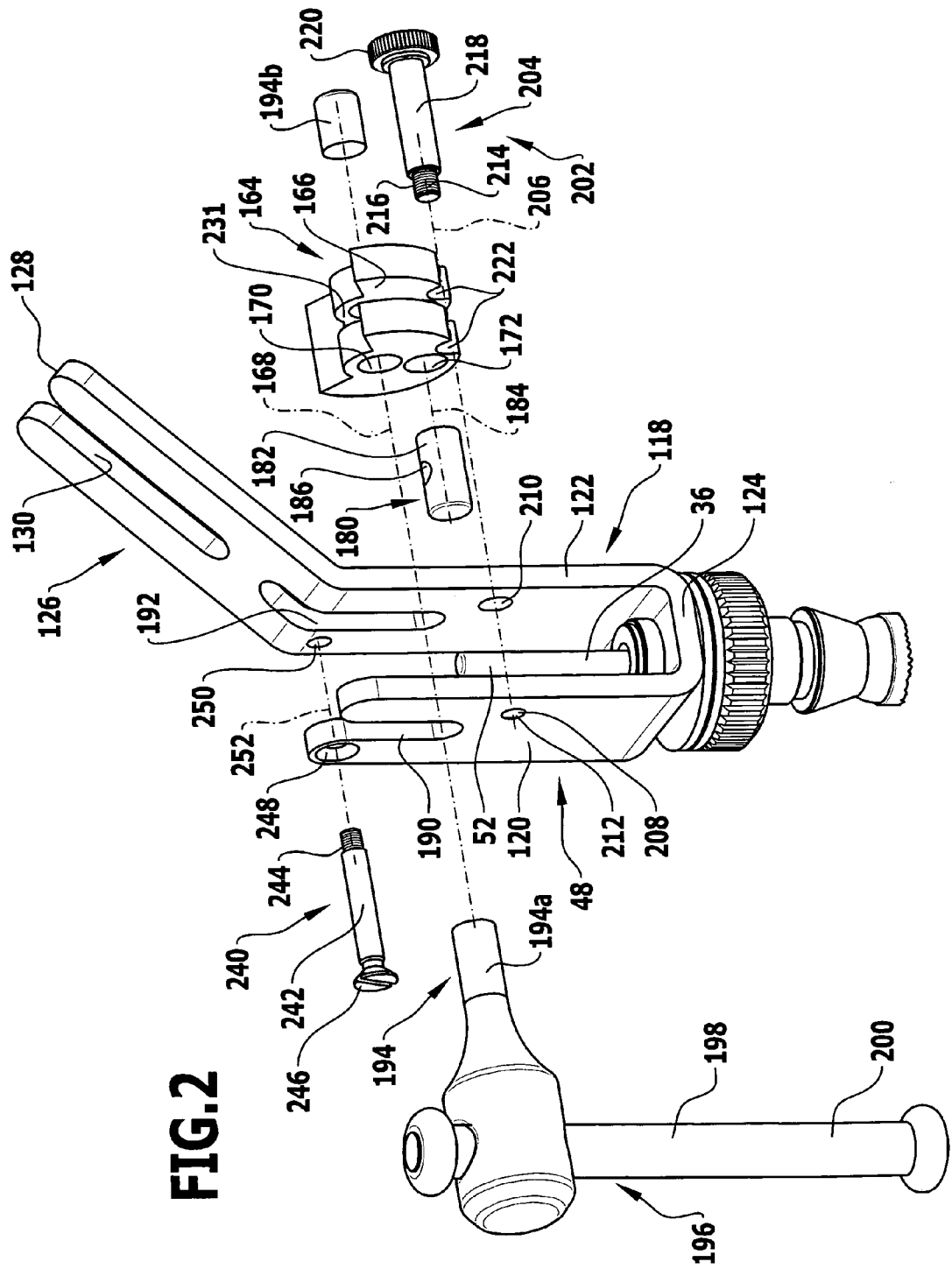
FIG. 2: shows an exploded illustration of a proximal end of the holding arm in the cleaning position.
Figure 3:
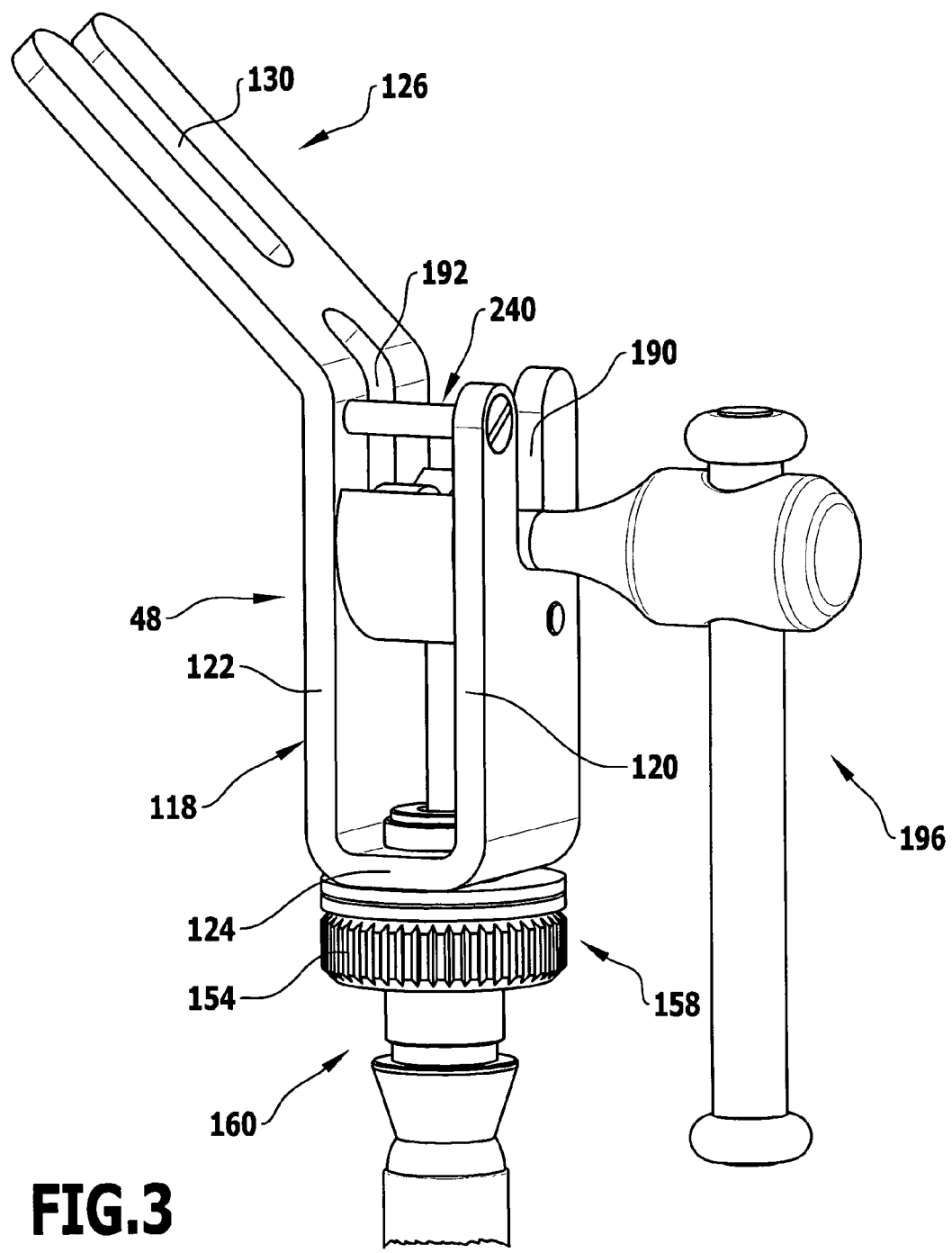
FIG. 3: shows a perspective view of the proximal end of the holding arm in the cleaning position.
Figure 4:
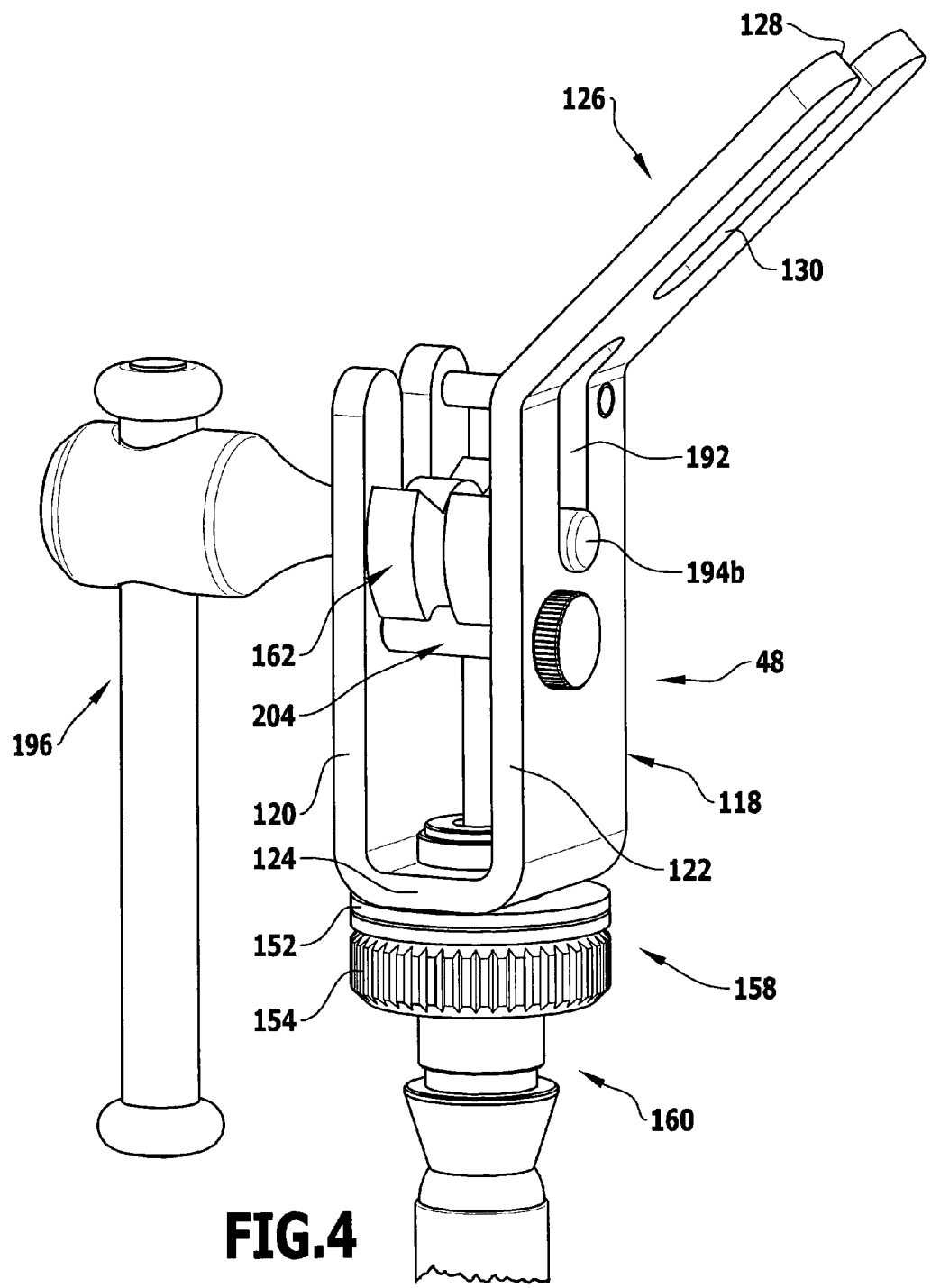
FIG. 4: shows a view analogous to FIG. 3 from the other side.
Figure 5:
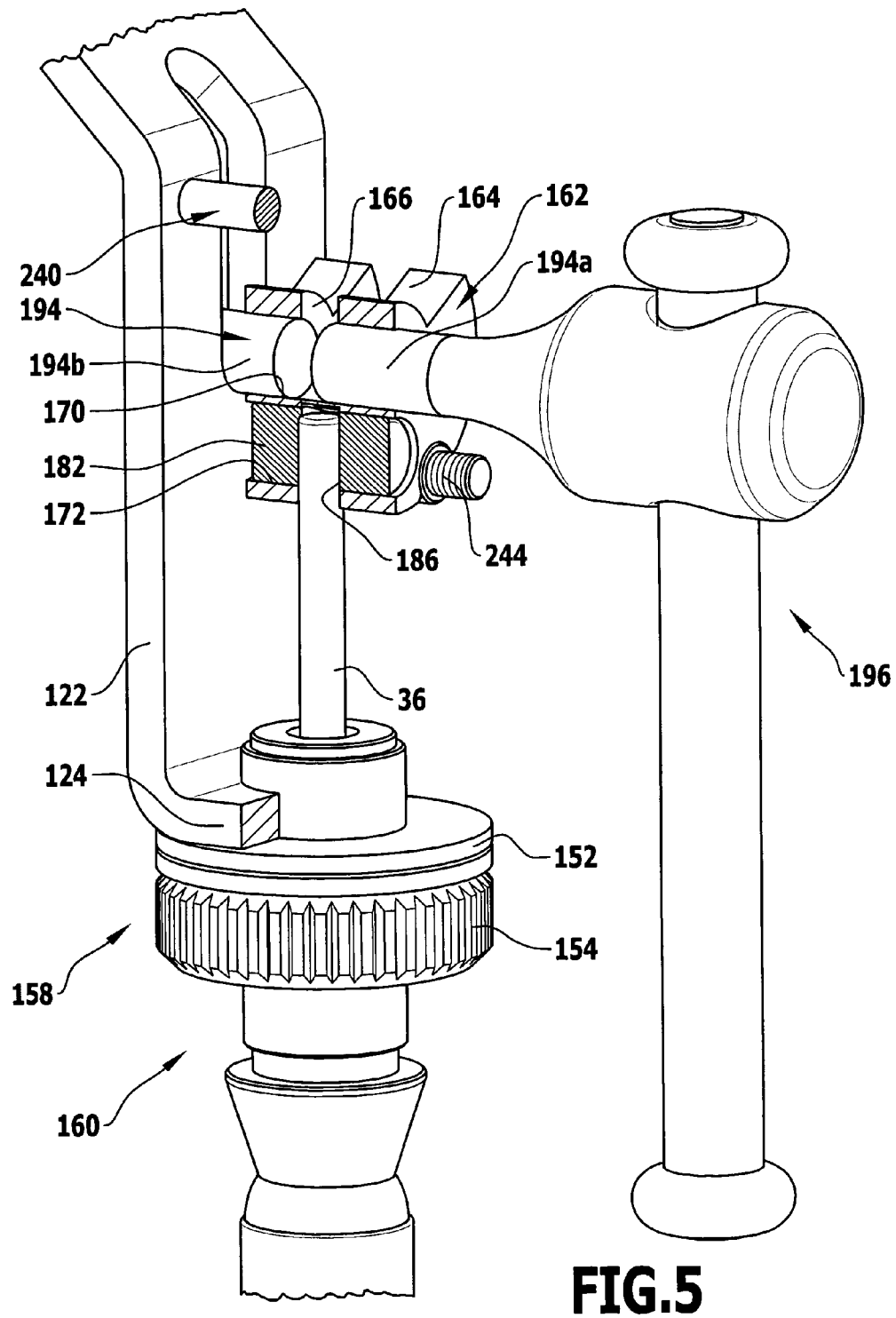
FIG. 5: shows an enlarged sectional view, partially cut away, of the illustration in FIG. 3.
Figure 6:
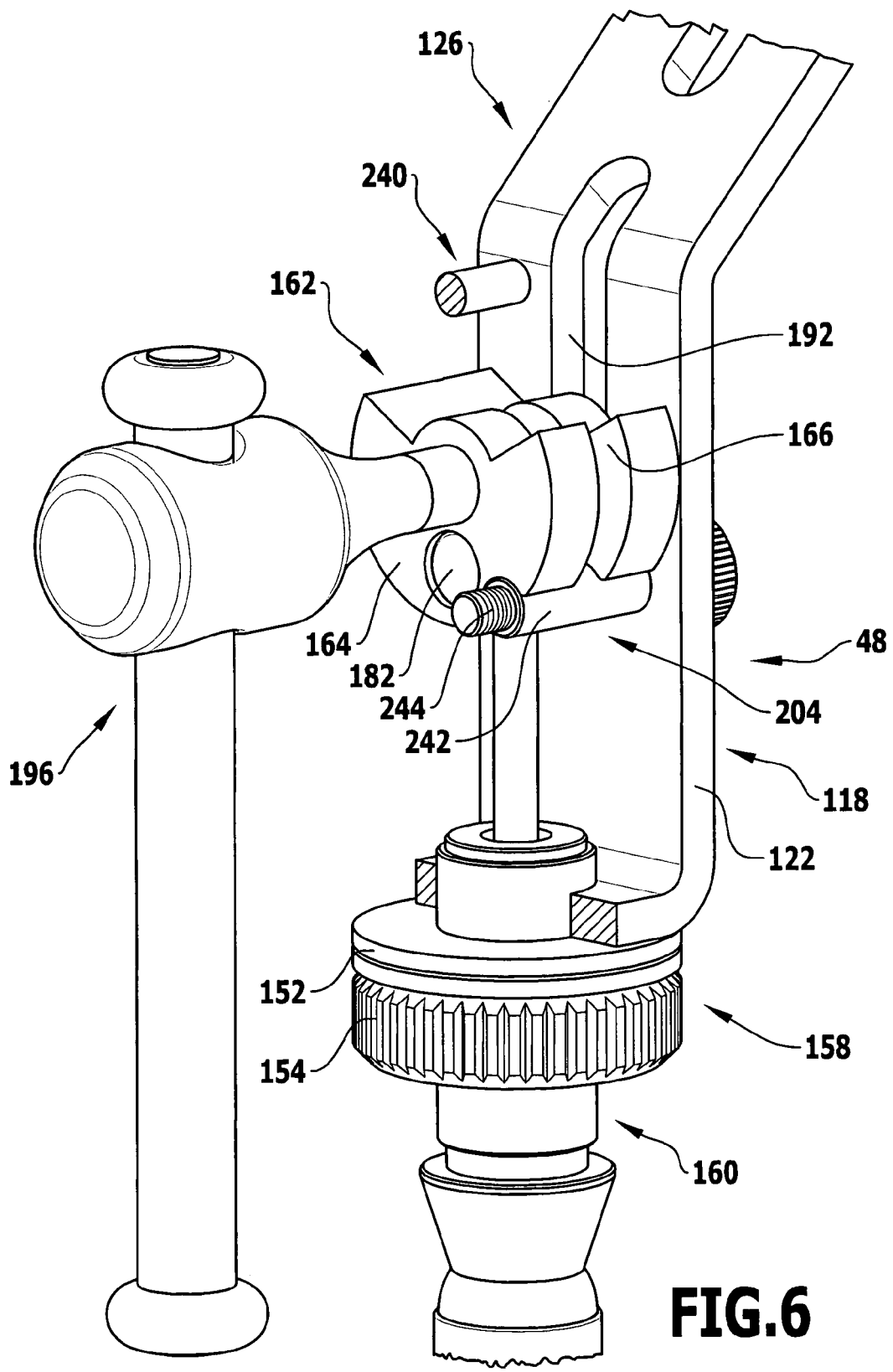
FIG. 6: shows a perspective partial view, partially cut away, of the proximal end of the holding arm.
Figure 7:
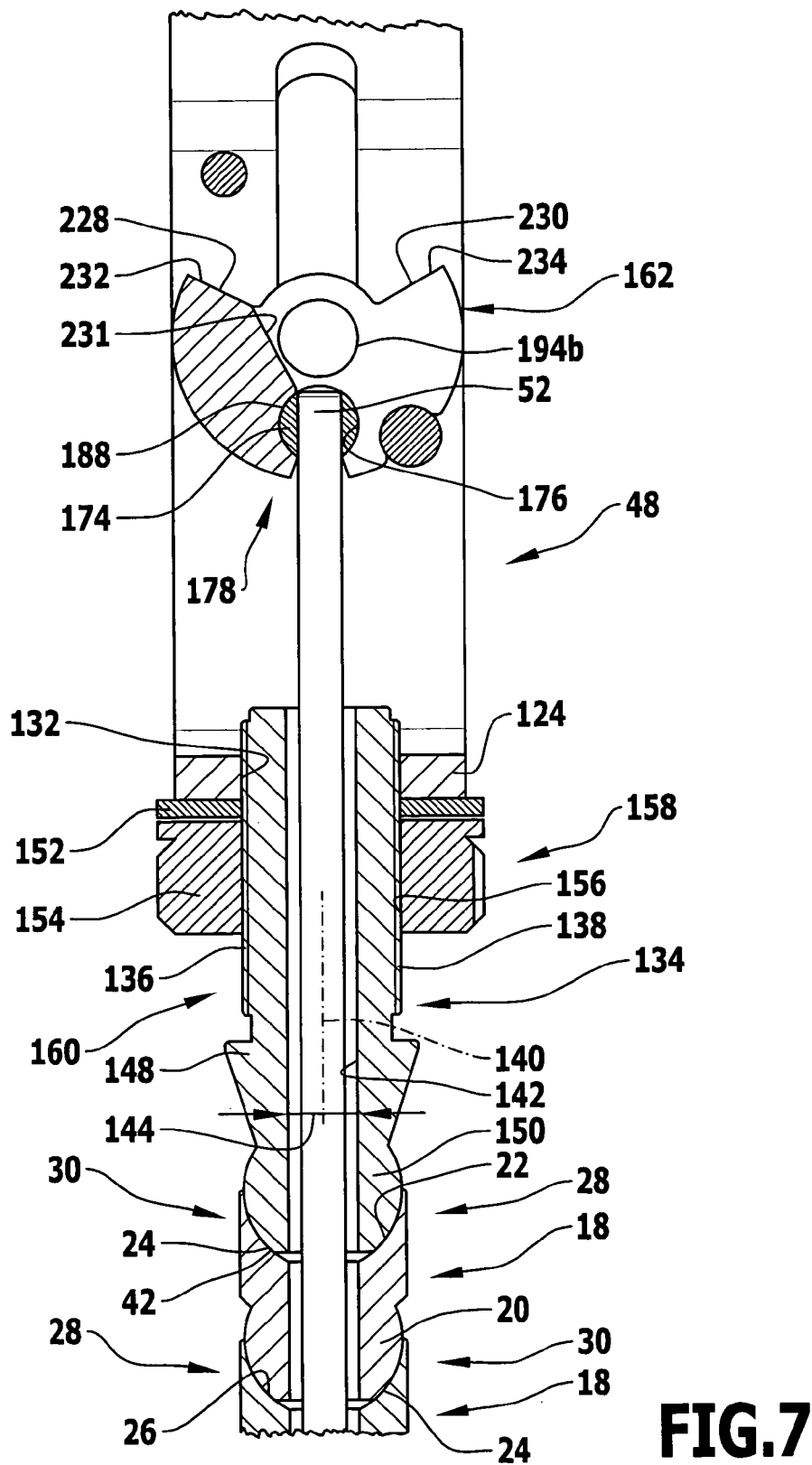
FIG. 7: shows a sectional view through the proximal end of the holding arm in the cleaning position.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical holding arm with a plurality of holding arm members coupled to one another and a tensioning device for tensioning the holding arm members against one another, wherein the tensioning device is designed in such a manner that the holding arm is adapted to be brought from an operative position, the holding arm members being tensioned against one another so as to be immovable in said operative position, into an adjusting position, the holding arm members being movable relative to one another in said adjusting position, wherein the holding arm is adapted, in addition, to be brought into a cleaning position, adjacent holding arm members being movable away from one another further in said cleaning position than in the adjusting position.

The transfer of the holding arm into the cleaning position makes it possible for the individual holding arm members to be moved away from one another to such an extent, i.e., for a space between them to be increased in size such that a defined and reliable cleaning as well as sterilization of the holding arm is possible, in contrast to the holding arms currently available on the market. In this respect, gap widths of at least one millimeter can preferably be achieved between the holding members. In addition, the holding arm is favorably designed such that it does not fall apart in the cleaning position, i.e., that it cannot be unintentionally separated into its individual parts. In order to be able to align the holding arm in a desired manner, it can be transferred from the operative position into the adjusting position. For an optimized handling, i.e., a quick tensioning of the holding arm members against one another, only minimal distances between the individual holding arm members are, however, preferably desired in the adjusting position and these are just adequate enough to move the holding arm members, which are in contact with one another in the operative position, relative to one another. These minimal distances are not, however, sufficient to ensure a qualified and defined cleaning, in particular an automatic cleaning in a rinsing machine. This is, however, exactly what is made possible by the tensioning device designed according to the invention which makes it possible to alter the maximum distance between the distal and the proximal end stops in such a manner that this is greater, preferably considerably greater, in the cleaning position than in the adjusting position.

It is advantageous when the tensioning device comprises a proximal and a distal end stop and when a maximum distance between the distal and the proximal end stops is greater in the cleaning position than in the adjusting position. The distance between the distal and the proximal end stops can be minimal in the operative position, in particular.

The holding arm members may be tensioned against one another in a simple manner when the tensioning device comprises a tensioning element which passes through the holding arm members.

The tensioning element is preferably designed in the form of a cable line. The cable line can, for example, be a wire cable or a wire strand which have a high tensile strength.

So that the holding arm can be transferred in a simple manner from the operative position into the adjusting position and vice versa, it is advantageous when a free length of the tensioning element between the proximal and the distal end stops can be varied with the tensioning device. Particularly when the holding arm members are threaded like pearls on the tensioning element, they can be moved relative to one another, for example, away from one another or towards one another when a free length of the tensioning element between the proximal and the distal end stops allows this, i.e., in particular in the cleaning position.

The construction of the tensioning device will be particularly simple when this comprises a distal tensioning part and a proximal tensioning part and when a distal end of the tensioning element is mounted and/or held on the distal tensioning part and a proximal end of the tensioning element on the proximal tensioning part. This makes it possible for the tensioning element to be mounted on the respective tensioning parts on the distal side and the proximal side. The distal tensioning part preferably comprises the distal end stop and the proximal tensioning part the proximal end stop.

In order to ensure that the distal end of the tensioning element cannot be released from the distal tensioning part, especially not in the cleaning position, it is favorable when the surgical holding arm comprises a securing device for securing the distal end of the tensioning element on the distal tensioning part in a securing position.

The securing device can preferably be brought from the securing position into a release position, in which the distal end of the tensioning element can be separated or released from the distal tensioning part. For example, the surgical holding arm may be completely disassembled in this way, in particular the holding arm members released from the tensioning element when they are threaded onto it. This may be desired or necessary for cleaning or maintenance purposes.

The construction of the securing device will be particularly simple when it comprises a securing element which can be releasably connected to the distal tensioning part. For example, it can be connected to the distal tensioning part in a connecting position and thus secure the distal end of the tensioning element on the distal tensioning part.

It is advantageous when the securing element can be screwed to the distal tensioning part or connected to it by a bayonet closure. In this way, it can be released from the distal tensioning part easily and quickly and also connected to it again in order to be able to secure the distal end of the tensioning element on the distal tensioning part or release it from the tensioning element again. The securing element advantageously comprises at least one flushing opening which forms a fluid connection between the surroundings of the holding arm and an interior space of the securing element which has the tensioning element passing through it. It is thus possible for cleaning fluids, in particular hot steam, as well, to act on the tensioning element in the area of the securing element in the cleaning position.

In accordance with an additional preferred embodiment of the invention, it may be provided for the securing element to close a distal tensioning element receptacle on the distal tensioning part at least partially in a connecting position, in which it is connected to the distal tensioning part, and to release the tensioning element receptacle in a separating position, in which it is separated from the distal tensioning part, in order to bring the tensioning element and the distal tensioning part into or out of engagement. This configuration allows the tensioning element receptacle to be opened in a simple manner by releasing the securing element from the distal tensioning part and, vice versa, to also close it again in order to release the tensioning element from the distal tensioning part and connect it to it again.

In order to be able to connect the tensioning element to the distal tensioning part in a simple and defined manner, it is favorable when the tensioning element comprises a distal holding member which can be brought into engagement with the distal tensioning element receptacle in a force and/or form locking manner. The distal holding member can thus be suspended, for example, in the tensioning element receptacle simply, securely and in a defined manner.

The construction of the distal tensioning part will be particularly simple when the distal tensioning element receptacle is designed in the form of an opening in the distal tensioning part.

The tensioning element can be introduced into the tensioning element receptacle and secured in it in a simple manner when the distal tensioning element receptacle has a lateral insertion opening which opens the tensioning element receptacle to the side in a direction transverse to a longitudinal direction defined by the distal tensioning element receptacle.

It may, in addition, be advantageous when the securing device is designed in such a manner that the securing position and/or the release position can be taken up in the operative position and/or in the adjusting position and/or in the cleaning position. The tensioning element can thus be secured on the distal tensioning part in a defined manner irrespective of the position, in which the holding arm is located.

The holding arm advantageously comprises a coupling device for coupling the proximal end of the tensioning element to the proximal tensioning part. The coupling device makes it possible for the proximal end of the tensioning element to be held on the proximal tensioning part in a defined manner.

The construction of the coupling device will be particularly simple when this comprises first and second coupling members which are formed or arranged on the proximal tensioning part and on the tensioning element and are in engagement with one another in a force and/or form locking manner in a coupling position.

The first and second coupling members can preferably be moved relative to one another in the coupling position. It is favorable when they can be rotated or pivoted about a common axis of rotation or pivot axis.

The first coupling member is favorably designed in the form of a coupling projection and the second coupling member in the form of a corresponding coupling recess. This configuration makes it possible for the coupling members to be brought into engagement with one another in a simple and reliable manner.

It is favorable when the tensioning device comprises a tensioning member which is held on the proximal tensioning part so as to be movable and can be coupled to the proximal end of the tensioning element. The tensioning member can be designed, in particular, to vary a free length of the tensioning element between the proximal and the distal end stops as a result of movement relative to the proximal tensioning part.

So that movement of the tensioning member relative to the proximal tensioning part can directly cause an alteration in length of a free length of the tensioning element between the end stops, it is advantageous when the tensioning member comprises the first or the second coupling member. As a result, it can be connected or coupled directly to the proximal end of the tensioning element.

A distance between the first or second coupling member comprised by the tensioning member and the proximal end stop can advantageously be altered. This allows a free length of the tensioning element between the distal and the proximal end stops to be altered in a simple manner on account of an alteration in the distance of the coupling member comprised by the tensioning member.

The handling of the surgical holding arm will be particularly simple when the tensioning member is arranged on the proximal side of the proximal end stop. The proximal end stop can be formed on the proximal tensioning part so as to be, in particular, stationary or movable.

The tensioning member is preferably mounted for rotation about an axis of rotation which extends transversely to a longitudinal axis defined by the proximal tensioning part. The transfer of the holding arm from the adjusting position into the operative position and vice versa can thus be brought about in a simple manner on account of rotation of the tensioning member about the axis of rotation.

In order to alter the distance between the distal and the proximal end stops in a simple manner, i.e., in particular a free length of the tensioning element between the end stops, it is advantageous when the first or second coupling member comprised by the tensioning member is arranged or designed to be spaced from the axis of rotation and is rotatable about the axis of rotation. Such an eccentric arrangement of the coupling member makes an alteration in the distance thereof from the proximal end stop possible as a direct result of rotation of the tensioning member about the axis of rotation.

So that an operator can handle the holding arm easily and reliably, in particular tension the holding arm members against one another in the operative position, it is advantageous when the holding arm comprises an actuating element which is coupled to the tensioning member for moving the same relative to the proximal tensioning part.

The construction of the actuating element will be particularly simple when it is designed in the form of a toggle.

In accordance with an additional preferred embodiment of the invention, the surgical holding arm can comprise a movement limiting device for limiting movement of the tensioning member relative to the proximal tensioning part. The movement limiting device can be designed and arranged, in particular, for defining the operative position, the adjusting position and/or the cleaning position.

The movement limiting device is advantageously designed in such a manner that, in a first limiting position, the tensioning member can be brought from the operative position into the adjusting position and vice versa. In particular, it can be ensured in the first limiting position that the tensioning member cannot be brought into the cleaning position either from the operative position or from the adjusting position without an alteration being made to the holding arm, for example, the actuation or removal of a corresponding part thereof.

It is advantageous when the movement limiting device is designed in such a manner that, in a second limiting position, the tensioning member can be secured on the proximal tensioning part so as to be immovable or essentially immovable in the cleaning position. This configuration of the movement limiting device ensures that the desired free length of the tensioning element between the distal and the proximal end stops, which is, in certain circumstances, required, in particular, for cleaning purposes, can be maintained.

It is favorable when the movement limiting device comprises at least one movement limiting member which interacts with the tensioning member in the first and/or second limiting position. For example, the movement limiting member can form a stop for correspondingly designed stop surfaces on the tensioning member and thus define the operative position and/or the adjusting position and/or the cleaning position in a simple and defined manner when coming into contact with the tensioning member.

The at least one movement limiting member is preferably in engagement with the tensioning member in a force and/or form locking manner in the cleaning position. In this way, it is possible to prevent the tensioning member from moving in the cleaning position and, in particular, a free length of the tensioning element between the end stops from being altered which could have a negative influence on the result of cleaning the holding arm.

According to an additional preferred embodiment of the invention, it may be provided for the movement limiting device to comprise first and second stops which interact with the at least one movement limiting member and for the movement limiting member and one of the stops to be in contact with one another in the adjusting position. In this way, it can be ensured that a distance between the end stops can be altered only such that movability of the holding arm members relative to one another is made possible.

The tensioning member favorably has a first recess, in which the movement limiting member engages in the cleaning position. It is thus possible to secure the tensioning member on the proximal tensioning part so as to be immovable or essentially immovable in the cleaning position.

Furthermore, the tensioning member can advantageously have a second recess which defines the first and second stops of the movement limiting device. In particular, the second recess can be designed such that the tensioning member is movable in such a manner that it can be brought into contact with the at least one movement limiting member with the first and second stop, respectively.

The construction of the movement limiting device will be particularly simple when the at least one movement limiting member is designed in the form of a bolt which can be releasably connected to the proximal tensioning part. The bolt therefore forms a stop, in particular in the form of a projection which can take up one or more defined positions on the proximal tensioning part. The bolt can, in particular, be designed so as to be screwed to the proximal tensioning part or connected to it by means of a bayonet closure.

In accordance with an additional preferred embodiment of the invention, it may be provided for the movement limiting member and the tensioning member to be brought out of engagement in order to transfer the holding arm from the adjusting position into the cleaning position and vice versa. For example, the movement limiting member can engage in the second recess but must, so that it can engage in the first recess, be brought out of engagement with the tensioning member first of all so that this can be moved in such a manner that the movement limiting member can be brought into engagement with the first recess.

The surgical holding arm advantageously comprises an adjusting device for altering a distance of the proximal end stop and the tensioning member relative to one another. With the adjusting device, a pretensioning of the tensioning element in the operative position can, in particular, be adjusted.

This is advantageous, in particular, because the tensioning element can lengthen somewhat during intensive use of the holding arm which could result in the holding arm members no longer being tensionable against one another so securely in the operative position that the holding arm has the rigidity required for its functioning. Furthermore, the adjusting device is advantageous for being able to utilize tensioning elements of different lengths. In particular, manufacturing tolerances during the production of the tensioning element can also be compensated for.

The adjusting device preferably comprises an adjusting member which is mounted on the proximal tensioning part so as to be movable in a longitudinal direction defined by it. In particular, the proximal end stop can be formed on the adjusting member.

The adjusting member can be moved relative to the proximal tensioning part in a simple and defined manner when it is mounted on the proximal tensioning part in a screwable manner. For example, it can be designed in the form of a knurled nut or in the form of a knurled screw with a bore through it, each of which can have the tensioning element passing through it.

In order to achieve a particularly stable construction of the holding arm, it is favorable when the proximal tensioning part comprises a bearing member, on which the tensioning member and the proximal end stop are arranged, mounted or formed.

So that the surgical holding arm can, for example, be secured to an operating table or a holding device attached thereto and, in addition, can be connected at its other end to an instrument, a tool or a surgical device, it is favorable when the distal tensioning part and the proximal tensioning part each comprise at least one coupling element for connecting the holding arm to corresponding coupling elements of surgical holding devices and/or surgical instruments and/or surgical tools and/or surgical equipment. The coupling elements can be designed, in particular, in the form of projections or recesses which can be brought into engagement with coupling elements, which are designed accordingly, in a force and/or form locking manner.

It is advantageous when a holding arm member joint is formed at least between two adjacent holding arm members. In this way, a movable holding arm can be formed.

The movability of the holding arm can be increased and improved in a simple manner when a holding arm member joint is formed between all adjacent holding arm members.

In order to be able to specify every possible desired shape of the holding arm, it is favorable when the holding arm member joint or when the holding arm member joints are designed in the form of ball-and-socket joints or hinge joints.

In accordance with an additional preferred embodiment of the invention, it may be provided for each holding arm member to define a first and a second joint surface and for the holding arm members to be arranged in such a manner that the at least one holding arm member joint comprises the first and second joint surfaces. This configuration makes it possible to define and design the holding arm member joints directly by way of joint surfaces of the holding arm members which abut on one another.

For example, a ball-and-socket joint can be formed in a simple manner between two adjacent holding arm members when the first joint surface is of a spherical design and when the second joint surface is designed as a hollow sphere.

The first joint surfaces are preferably tensioned against the second joint surfaces in the operative position. As a result, any movement between adjacent holding arm members can be prevented. In particular, the first and second joint surfaces can be provided with a macroscopic surface structure in order to be able to ensure holding forces which are as large as possible when the holding arm takes up the operative position.

The first and second joint surfaces are preferably movable relative to one another in the adjusting position. As a result, relative orientations of adjacent holding arm members can be altered in a simple manner in the adjusting position.

In order to be able to clean the joint surfaces, in particular, in a reliable manner, it is advantageous when the first and second joint surfaces can be moved away from one another in the adjusting position and in the cleaning position. In the cleaning position, they can preferably be moved away from one another by at least 1 mm. They can preferably be moved away from one another to such an extent that in a side view projections of adjacent holding arm members no longer touch one another, not even when they abut on one another in the operative position in a form locking or essentially form locking manner.

The invention also relates to a surgical holding device for holding and securing surgical instruments and/or surgical tools and/or surgical equipment, comprising at least one holding arm with a plurality of holding arm members coupled to one another and a tensioning device for tensioning the holding arm members against one another, wherein the tensioning device is designed in such a manner that the holding arm is adapted to be brought from an operative position, the holding arm members being tensioned against one another so as to be immovable in said operative position, into an adjusting position, the holding arm members being moveable relative to one another in said adjusting position, wherein the holding arm is, in addition, adapted to be brought into a cleaning position, adjacent holding arm members being movable away from one another further in said cleaning position than in the adjusting position.

The holding arm is favorably designed in the form of one of the holding arms described above. The holding arm then has the advantages described in conjunction with preferred embodiments.

Part of a surgical holding device 10 is illustrated by way of example in FIG. 1, namely a surgical holding arm 12 which can be secured, for example, to an operating table with a distal end 14 and can be connected at a proximal end 16, for example, to an instrument, a tool or equipment of a medical or surgical nature.

The holding arm 12 comprises a plurality of holding arm members 18 which are coupled to one another and are of an identical design. They comprise a spherical end 20 as well as an end 22 which is a hollow sphere. The spherical end 20 and the hollow sphere end 22 are of a corresponding design so that the spherical end 20 can be brought into engagement with the hollow sphere end 22 with a first, spherical joint surface 24 in such a manner that a second, hollow sphere joint surface 26 of the hollow sphere end 22 is areally in contact with the first joint surface 24. A holding arm member joint 28 is thus formed between two adjacent holding arm members 18, namely in the form of a ball-and-socket joint 30.

The holding arm 12 comprises a tensioning device, which is designated as a whole with the reference numeral 32, for tensioning the holding arm members 18 against one another in an operative position. The tensioning device 32 is designed in such a manner that the holding arm 12 can be brought from the operative position, in which the holding arm members 18 are tensioned against one another so as to be immovable, into an adjusting position, in which the holding arm members 18 can be moved relative to one another. The tensioning device 32 comprises a tensioning element 34 in the form of a cable line 36 which passes through the pearl-like holding arm members 18. In order to be able to thread the holding arm members 18 onto the cable line 36 like pearls, they are each provided with a longitudinal bore 38 which defines a longitudinal axis 40. Each holding arm member 18 is designed to be rotationally symmetric to the longitudinal axis 40 thereof.

The tensioning device 32 comprises a proximal end stop 42 and a distal end stop 44. It is designed in such a manner that a free length of the tensioning element 34 between the end stops 42 and 44 can be varied, as will be explained in detail in the following.

The tensioning device 32 further comprises a distal tensioning part 46 and a proximal tensioning part 48. A distal end 50 of the cable line 36 is held on the distal tensioning part 46, a proximal end 52 of the cable line 36 on the proximal tensioning part 48. The distal tensioning part 46 comprises a cylindrical holding section 54 which has a longitudinal bore 56 passing through it which has an internal diameter 58 which is only slightly greater than an external diameter 60 of the cable line 36. The longitudinal bore 56 widens towards a distal end 62 for forming a widened area 74 in one step so that an annular surface 64 which points in a distal direction is formed. The distal end 50 of the cable line 36 forms a distal holding member 66 in the form of a cylindrical body which has an external diameter 68 which is adapted to an internal diameter 70 of the widened area 74 of the longitudinal bore 56. The holding section 54 is provided with a lateral slit 72 which opens the widened area 74 of the longitudinal bore 56 as well as the longitudinal bore 56 itself to the side in a direction transverse to a longitudinal direction 78, which is defined by the widened area 74 forming a distal tensioning element receptacle 76, and thus defines an insertion opening 80.

On this distal side, an insertion section 82 adjoins the holding section 54 and this has the shape of a semi-hollow cylindrical sleeve, the internal diameter of which corresponds to the internal diameter 70. At the distal end 86, transverse to the longitudinal axis 78, a cylindrical bolt projects transversely out of the widened area 74 which extends into the insertion section 82 and this bolt forms a distal coupling element 84, with which the holding arm can be secured, for example, to an operating table or to which an instrument or tool can be attached. A distance 88 between the annular surface 64 and the distal coupling element 84 is equal to or somewhat greater than a height 90 of the holding member 66 and so the holding member can be inserted laterally between the annular surface 64 and the distal coupling element 84.

A securing device designated as a whole with the reference numeral 92 serves the purpose of securing the distal end 50 of the tensioning element 34 on the distal tensioning part 46 in a securing position. The securing device comprises a securing element 94 in the form of a securing sleeve which can be releasably connected to the distal tensioning part 46. An annular groove 98, which is open in a radial direction, is formed on the distal tensioning part 46 adjacent to its proximal end 96. A securing projection 104 which corresponds to the annular groove is formed on an inner surface 100 of an annular wall 102 of the securing sleeve and has a width in circumferential direction which is not greater than a width 106 of the slit 72, wherein the width 106 corresponds to the internal diameter 58. The annular groove 98 in conjunction with the securing projection 104 forms a bayonet closure 108 and so the securing sleeve can be connected to the distal tensioning part 46 in such a manner that the distal end 110 of the securing sleeve is pushed over an end section 112 of the holding section 54 which projects in a proximal direction until the end 110 abuts on an annular surface 114 which points in a proximal direction. The end section 112 has a maximum external diameter which corresponds to an internal diameter of the securing element 92 in the area of its distal end. The securing element 94 can, however, be pushed over the end section 112 only when the securing projection 104 engages in the slit 72 at the same time. If the end 110 abuts on the surface 114, the securing element 94 can be turned about the longitudinal direction 78 and in this way the securing sleeve can be secured on the distal tensioning part 46.

A proximal end of the securing element 94 has a receptacle 116 which is a hollow sphere and is designed to correspond to the first joint surface 24 so that the spherical end 20 of a holding arm member 18 can be introduced into the receptacle 116. The receptacle 116 defines the distal end stop of the tensioning device 32 at the same time.

The securing element 94 is connected to the distal tensioning part 46 in a connecting position, in which the securing projection 104 engages in the annular groove 98. In this respect, it closes the distal tensioning element receptacle 76 partially. If the securing element 94 is released or separated from the distal tensioning part 46, it frees up the tensioning element receptacle 76. In this separated position, the tensioning element 34 can be coupled to the distal tensioning part 46. For this purpose, the distal end 50 of the tensioning element 34 will, first of all, be pushed through the securing element 94. Subsequently, the tensioning element 34 will be pushed in a distal direction to such an extent until the holding member 66 abuts on the distal coupling element 94. In this position, the cable line 36 can be introduced laterally through the distal tensioning element receptacle 76 and be aligned coaxially to the longitudinal direction 78. If the tensioning element 34 is now drawn in a proximal direction, the holding member 66 can engage in the widened area 74 in a form locking manner. If, in a next step, the securing element 94 is coupled to the distal tensioning part 46 as a result of the securing projection 104 being brought into engagement in the annular groove 98, the tensioning element 34 is secured on the distal tensioning part 46 since it cannot be separated from the distal tensioning part 46 either in a distal direction or in a proximal direction. As a result of the fact that the securing element 94 closes the distal tensioning element receptacle 76 partially, it is also not possible to move the cable line 36 laterally out of the distal tensioning element receptacle through the insertion opening 80. It is, therefore, possible altogether to bring the securing device 42 from the securing position into a release position, in which the distal end of the tensioning element 34 can be separated or released from the distal tensioning part 46.

So that a cleaning fluid can also penetrate the longitudinal bore 56 in the area of the securing element 94 during cleaning of the holding arm 12 in the securing position, flushing openings 117 in the shape of elongated holes are formed on the securing element 94 distributed over the circumference and they form a fluid connection between the interior of the securing element 94 and the surroundings. Preferably, between 5 and 10 flushing openings 117 are formed.

The proximal tensioning part 28 comprises a bearing member 188 which is essentially U-shaped and has a first plate-like bearing arm 120, a second plate-like bearing arm 122 which extends parallel thereto and a connecting plate 124 which connects the two bearing arms 120 and 122 to one another on the distal side and extends transversely thereto. A plate-like coupling element 126, which projects at an angle of approximately 45°, is arranged, i.e., connected in one piece to the bearing member 118 at a proximal end of the bearing arm 122. A coupling slit 130 extends from a free end 128 of the coupling element 126 over approximately ⅔ of an overall length of the coupling element 126 in the direction towards the bearing arm 122. The coupling element 126 can be connected in a force and/or form locking manner to an operating table or to instruments, tools or surgical or medical equipment.

The connecting plate 124 is provided with a bore 132, into which a holding arm member adapter 134 with a proximal end section 136 is introduced which is provided with an external thread 138. The holding arm member adapter 134 is, altogether, designed to be rotationally symmetric to a longitudinal axis 140 and, coaxial thereto, is provided with a bore 142, the internal diameter 144 of which corresponds to an internal diameter 146 of the holding arm members 18 which is somewhat greater than the external diameter 68 of the holding member 66.

On the distal side, a central section 148 adjoins the end section 136 and this is designed in the form of a truncated cone which narrows in a distal direction. A spherical end 150 adjoins the central section 148 on the distal side and this is designed, in accordance with the spherical ends 20 of the holding arm members 18, with a first joint surface 24 corresponding to the second joint surface 26 of the holding arm member 18 which is in engagement with the holding arm member adapter 134. On the distal side, a washer 152 abuts on the connecting plate 124. The holding arm member adapter 134 forms, together with the knurled nut 154 which has an internal thread 156 corresponding to the external thread 138, an adjusting device 158 for altering the distance between the end 150 and the connecting plate 124. The end 150 forms the proximal end stop for the holding arm members 18. The knurled nut 154 can be screwed onto the holding arm member adapter 134 and forms an adjusting member 160 which is mounted for movement parallel to the longitudinal axis 140.

The tensioning device 32 comprises a tensioning member 162 which is held on the proximal tensioning part 48 so as to be movable and can be coupled to the proximal end 52 of the tensioning element 32. The tensioning member 162 is designed in the form of an eccentric disk 164. It comprises an annular groove 166 which has a width which is somewhat greater than the external diameter 60 of the cable line 36. The tensioning member 162 defines a longitudinal axis 168 which is oriented transversely to the longitudinal axis 140 and is, coaxially thereto, provided with a bore 170. A receiving bore 172 is designed to be eccentric to the bore 170 and parallel thereto and forms a coupling member 174 in the form of a coupling recess 176. A coupling device designated altogether with the reference numeral 178 comprises a first coupling member 180 in the form of a cylindrical bolt 182 which can be inserted in a form locking manner into the coupling recess 176 which forms the second coupling member 174. It defines a longitudinal axis 184 and is provided at right angles thereto with a bore 186 which serves to accommodate the proximal end 52 of the cable line 36. The bolt 182 is pushed sideways into the coupling recess 176 and the end 52 into the bore 186. The cable line 36 is then connected non-releasably to the bolt 182. The bolt 182 therefore forms a coupling projection 188 which is in engagement with the coupling recess 176 in a form locking manner. The annular groove 166 opens the coupling recess 176 at right angles to the longitudinal axis 184 so that the cable line 36 projects from the first coupling member 180 through the annular groove 166. The bolt 182 is rotatable about the longitudinal axis 184 in a coupling position, in which the first and second coupling members 180 and 174 are in engagement in a form locking manner. The tensioning member 162 thus comprises the second coupling member 174.

The tensioning member 162 is mounted on the proximal tensioning part 48 for rotation about the longitudinal axis 168. For this purpose, the bearing arm 120 is provided with a bearing slit 190 in the same way as the bearing arm 122 is provided with a bearing slit 192 which extends parallel to the bearing slit 190 and extends somewhat further into the coupling element 126. A cylindrical bearing shaft 194 which is mounted in the bearing slits 190 and 192 so as to be rotatable and displaceable is designed in two parts, has an external diameter corresponding to the bore 170 and passes through it. A first bearing shaft part 194a projects somewhat beyond the tensioning member 162 and engages in the bearing slit 190; a second bearing shaft part 194b which is arranged and aligned flush with the first bearing shaft part 194a likewise projects somewhat beyond the tensioning member 162 and engages in the bearing slit 192. The bearing shaft 194 is, in addition, connected non-rotatably to the tensioning member 162 with the bearing shaft parts 194a and 194b forming it. A distance between end surfaces of the bearing shaft parts 194a and 194b which face one another corresponds to a width of the annular groove 166.

An actuating element 196 in the form of a toggle 198 is coupled non-rotatably to the bearing shaft 194, namely to the bearing shaft part 194a. When the toggle 198 is pivoted about the longitudinal axis 168, the tensioning member 162 is rotated at the same time about the longitudinal axis 168. As a result, a distance between the first coupling member 180 and the connecting plate 124 or the proximal end stop 42 will also, however, be altered.

A distance between the first coupling member 180 and the proximal end stop 42 will be minimal when the coupling recess 176 takes up its most distal position with respect to the longitudinal axis 168 and points in the direction towards the connecting plate 124, as illustrated in FIGS. 1 to 7. As a result of this, a free length of the cable line 36 between the end stops 42 and 44 is at a maximum. A movement limiting device 202 serves to limit movement of the tensioning member 162 relative to the proximal tensioning part 48. It comprises a movement limiting member 204 which is arranged and designed in such a manner that movement of the tensioning member 162 relative to the proximal tensioning part 48 will be limited at least partially or even completely restricted. The bearing arms 120 and 122 have a bore passing through them coaxially to a longitudinal axis 206 which extends parallel to the longitudinal axis 168, wherein a bore 208 passing through the bearing arm 120 has a smaller internal diameter than a bore 210 passing through the bearing arm 122. The bore 208 is provided with an internal thread 212 which is designed to correspond to an external thread 214 of a distal screw bolt section 216 of the movement limiting member 204. On the proximal side, a cylinder section 218, on which a head 220 having a greater external diameter is integrally formed, adjoins the screw bolt section 216. The movement limiting member 204 can be connected to the proximal tensioning part 48 in that the screw bolt section 216 is inserted through the bore 210 in the direction towards the bore 208 and is screwed to the internal thread 212.

A first recess 222 is provided on the eccentric disk 164 in the form of a groove which extends parallel to the longitudinal axis 168 and is open pointing away from it. It is designed to be coaxial to the longitudinal axis 206 and somewhat to the side of the receiving bore 172. The bores 208 and 210 are positioned such that the cylinder section 218 can engage in the recess 222 in a form locking manner. The tensioning member 162 is then non-rotatably secured on the proximal tensioning part 48 and takes up the cleaning position, in which the distance between the first coupling member 180 and the proximal end stop 42 is minimal.

A second recess 224 is formed on the tensioning member 162 and this defines an area of the tensioning member 162 which is free from annular grooves. It is designed to be symmetrical with respect to a plane 226 which contains the longitudinal axes 168 and 184 in the assembled state of the holding arm 12. Lateral limiting surfaces 232 and 234, each of which defines a plane containing the longitudinal axis 168 and which are inclined in relation to one another through an opening angle 236 of approximately 120°, form first and second stops 228 and 230 of the movement limiting device 202. In addition to the annular groove, a tensioning element guide slit 213 is designed to adjoin directly onto this and opens the tensioning member 162 in the area between the bearing shaft parts 194a and 194b, in addition, in order to be able to always tension the cable line 36 in a direct line towards a proximal end of the end section 136 irrespective of a position of the tensioning member 162. The tensioning element guide slit 213 therefore intersects the longitudinal axis 168.

So that the first and second stops 228 and 230 can interact with the movement limiting member 204, the latter, when it is in engagement with the recess 222 for defining the cleaning position, must be released first of all from the proximal tensioning part 48. If the movement limiting member 204 releases the tensioning member 162, the tensioning member 162 can be pivoted through approximately 90° by means of the toggle 198 so that the movement limiting member 204 can be screwed to the proximal tensioning part 48 again in the manner described above. The cylinder section 218 is now arranged within the second recess 224 and limits any movement of the tensioning member 162 about the longitudinal axis 168. Extreme positions of the tensioning member 162 are defined when the movement limiting member 204 comes into contact with the stops 228 and 230. If the cylinder section 218 abuts on the limiting surface 234, the holding arm 12 takes up the so-called adjusting position. A free length of the cable line 36 between the end stops 42 and 44 is clearly decreased in relation to the cleaning position, as illustrated schematically in FIG. 8. The holding arm members 18 may now be moved away from one another only to such an extent that a movable section of the holding arm 12, which is defined by the plurality of the holding arm members 18, can be shaped in the desired manner.

So that the tensioning member 162, which is mounted by means of the bearing shaft 194 so as to be rotatable and displaceable in the bearing slits 190 and 192, cannot be released from the proximal tensioning part 48 in an undesired manner, a securing bolt 240 is provided with an elongated, cylindrical section 242 which has at its distal end an external threaded section 244 which is somewhat reduced in size in its external diameter. A proximal end of the securing bolt 240 forms a flat head 246 with a screw slit. The bearing arm 120 is provided at its free end adjacent to the bearing slit 190 with a bore 248, the internal diameter of which is adapted to the external diameter of the section 242. The bore 248 defines a longitudinal axis which extends parallel to the longitudinal axis 206. The bearing arm 122 is likewise provided adjacent to the bearing slit 192 with a bore 250 which has an internal thread corresponding to the external threaded section 244. The securing bolt 240 can thus be pushed through the bore 248 with the external threaded section 244 first and be displaced in the direction towards the bore 250. Subsequently, the securing bolt 240 will be screwed to secure it to the bearing member 118. The section 242 extends between the bearing arms 120 and 122 in such a manner that the tensioning member 162 cannot be released from the proximal tensioning part 48 without the securing bolt 240 being removed.

Figure 8:
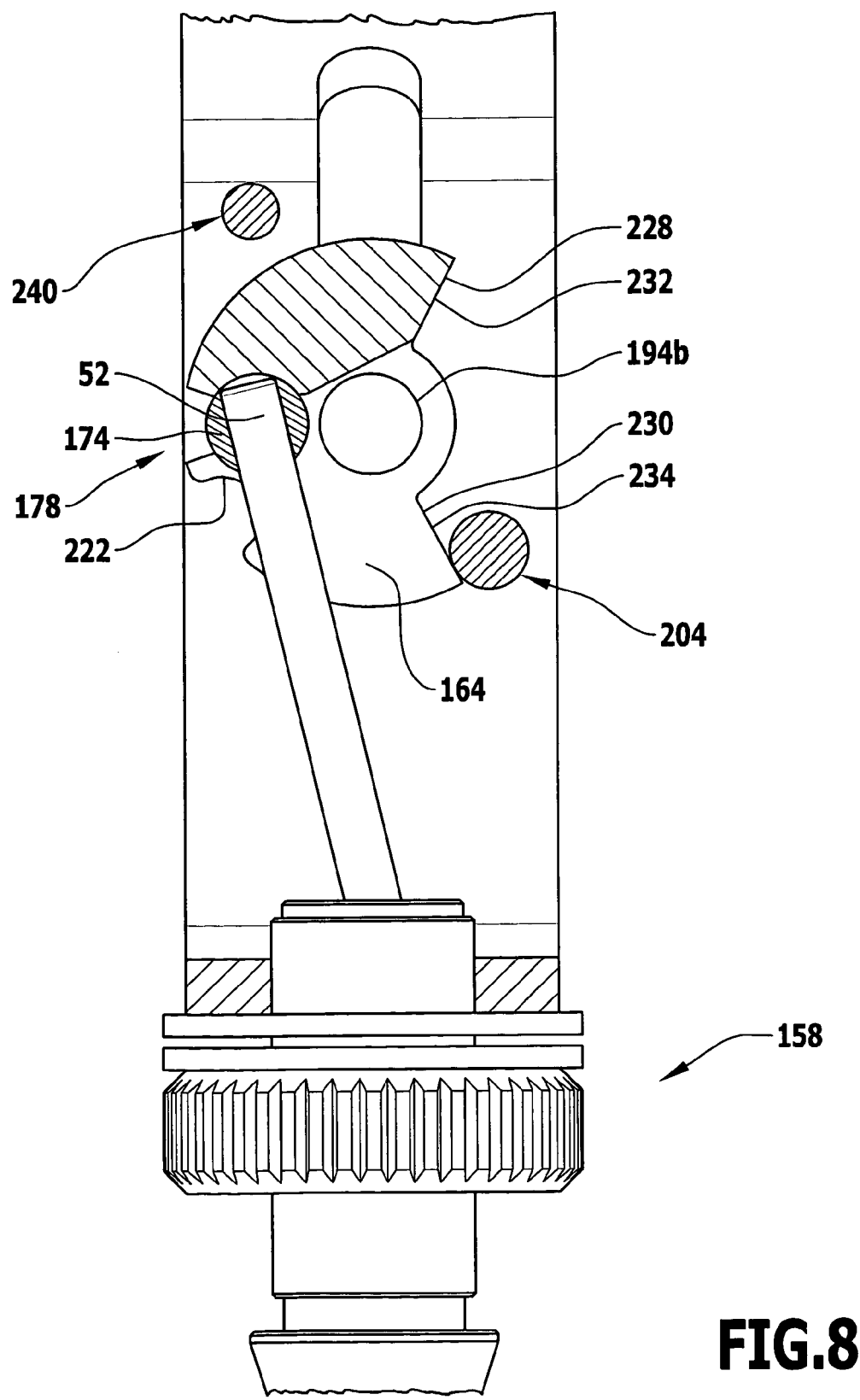
FIG. 8: shows a view analogous to FIG. 7 in the adjusting position.
Figure 9:
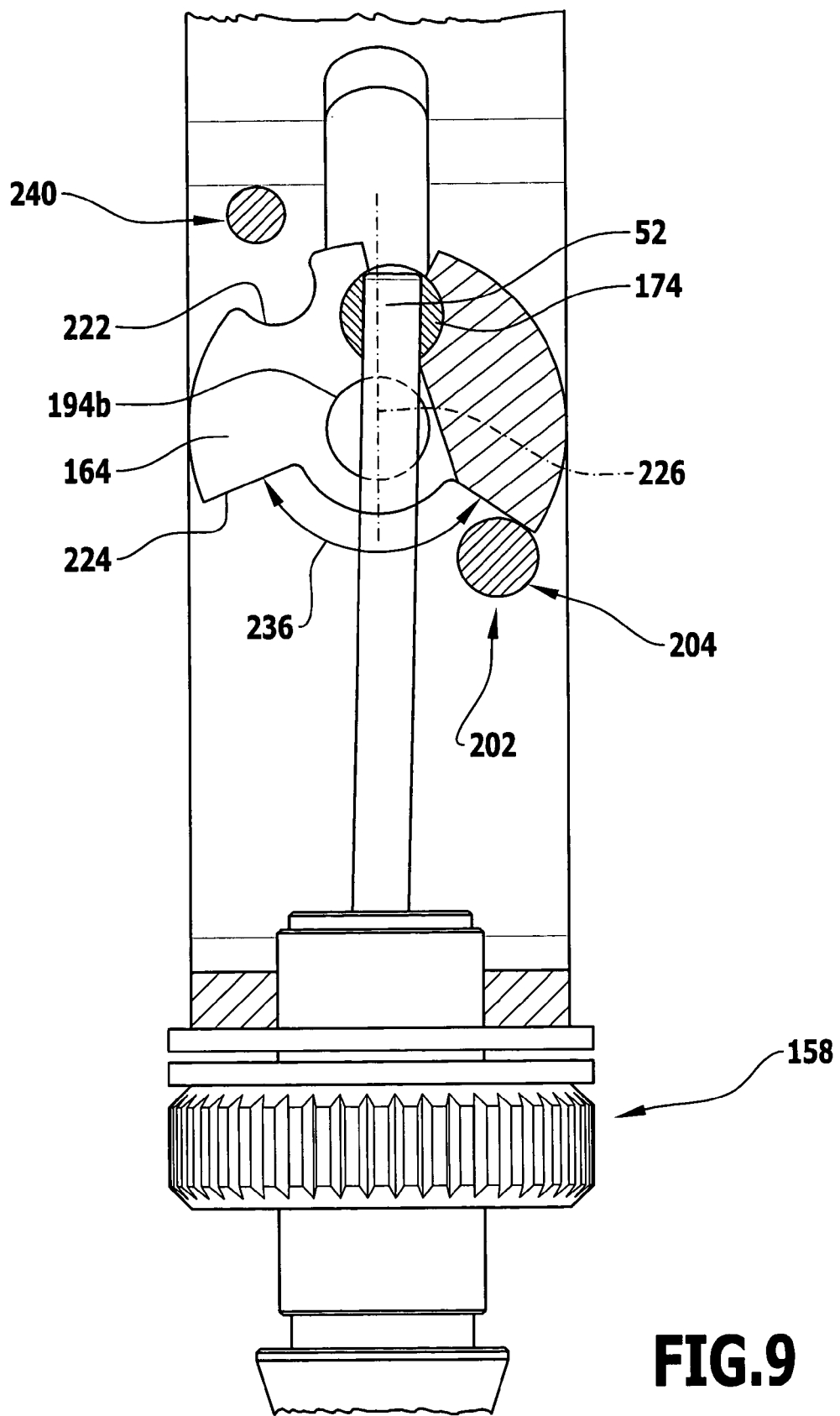
FIG. 9: shows a view analogous to FIG. 8 in the operative position.
Figure 10:
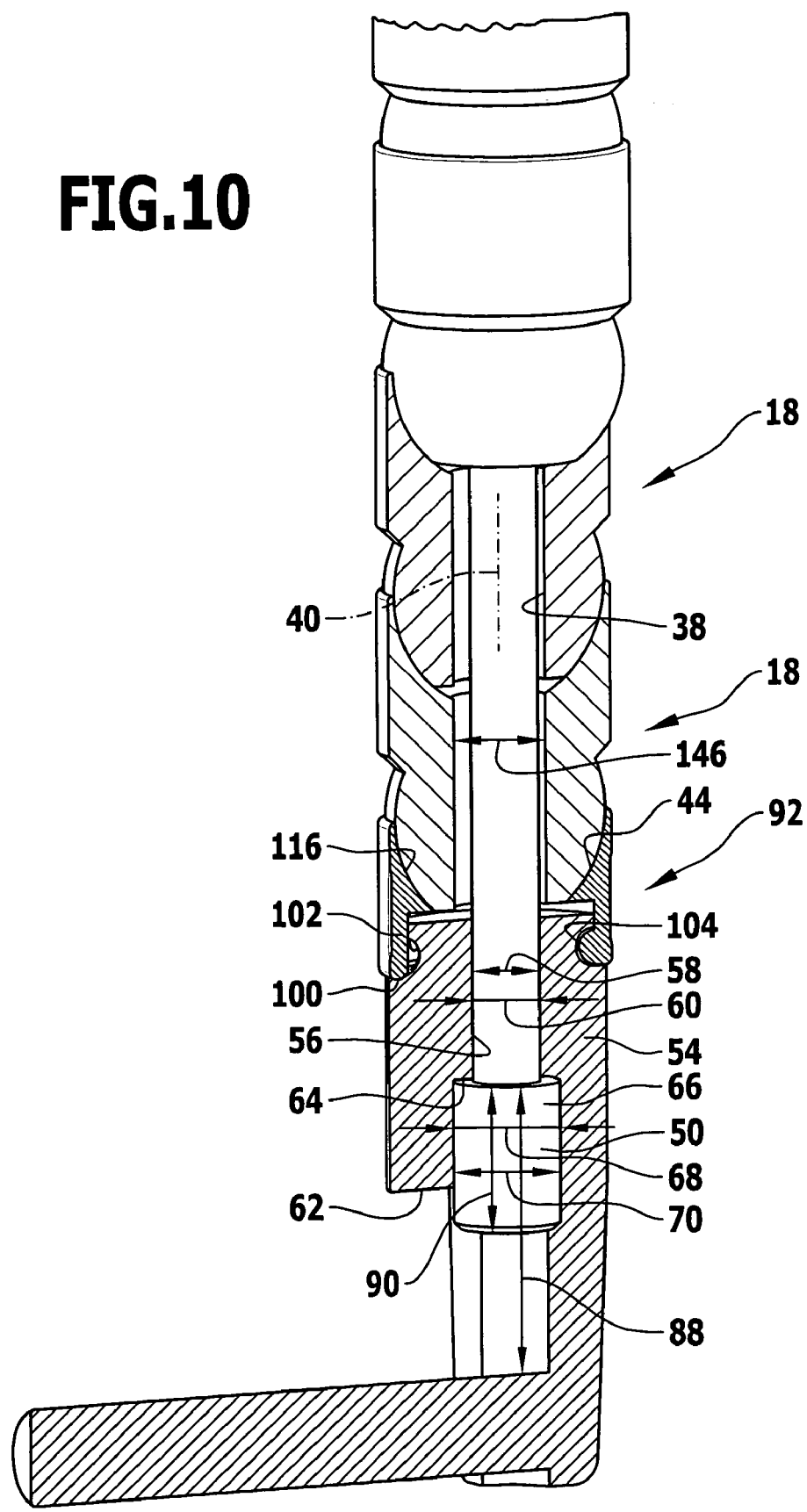
FIG. 10: shows a view, partially cut away, of a distal end of the holding arm in the operative position.
Figure 11:
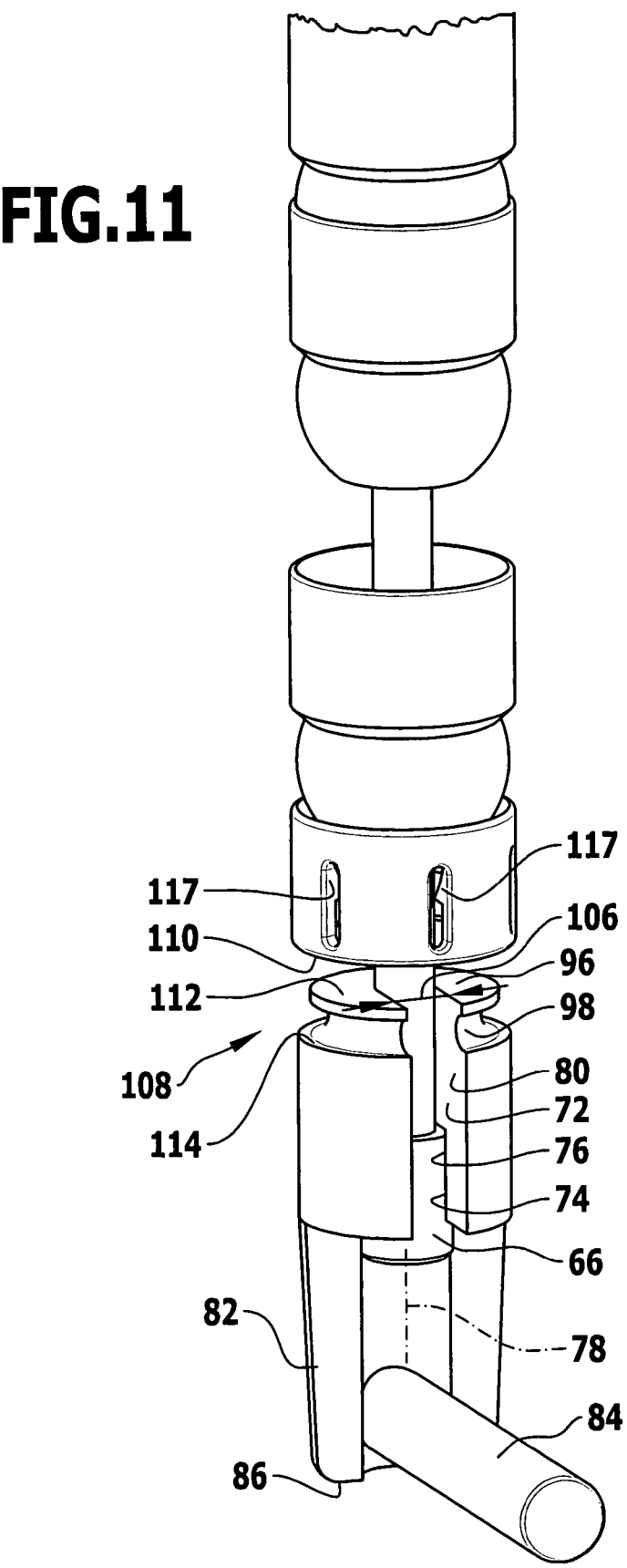
FIG. 11: shows a perspective view of the distal end of the holding arm in the cleaning position during the separation of the tensioning element from the distal tensioning part.
Figure 12:
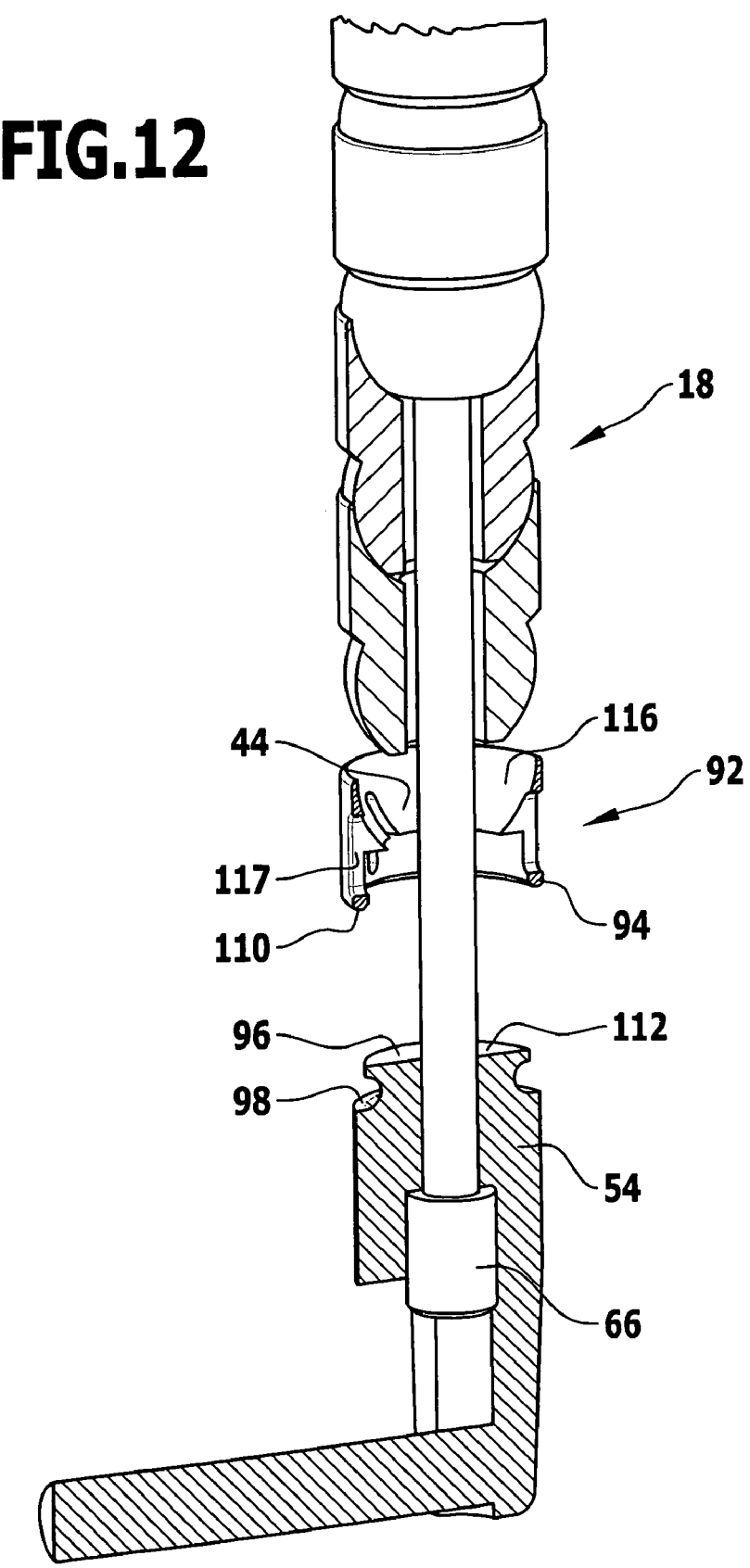
FIG. 12: shows a view, partially cut away, analogous to FIG. 10 of the holding arm in the cleaning position during the separation of the tensioning element from the distal tensioning part.
Figure 13:
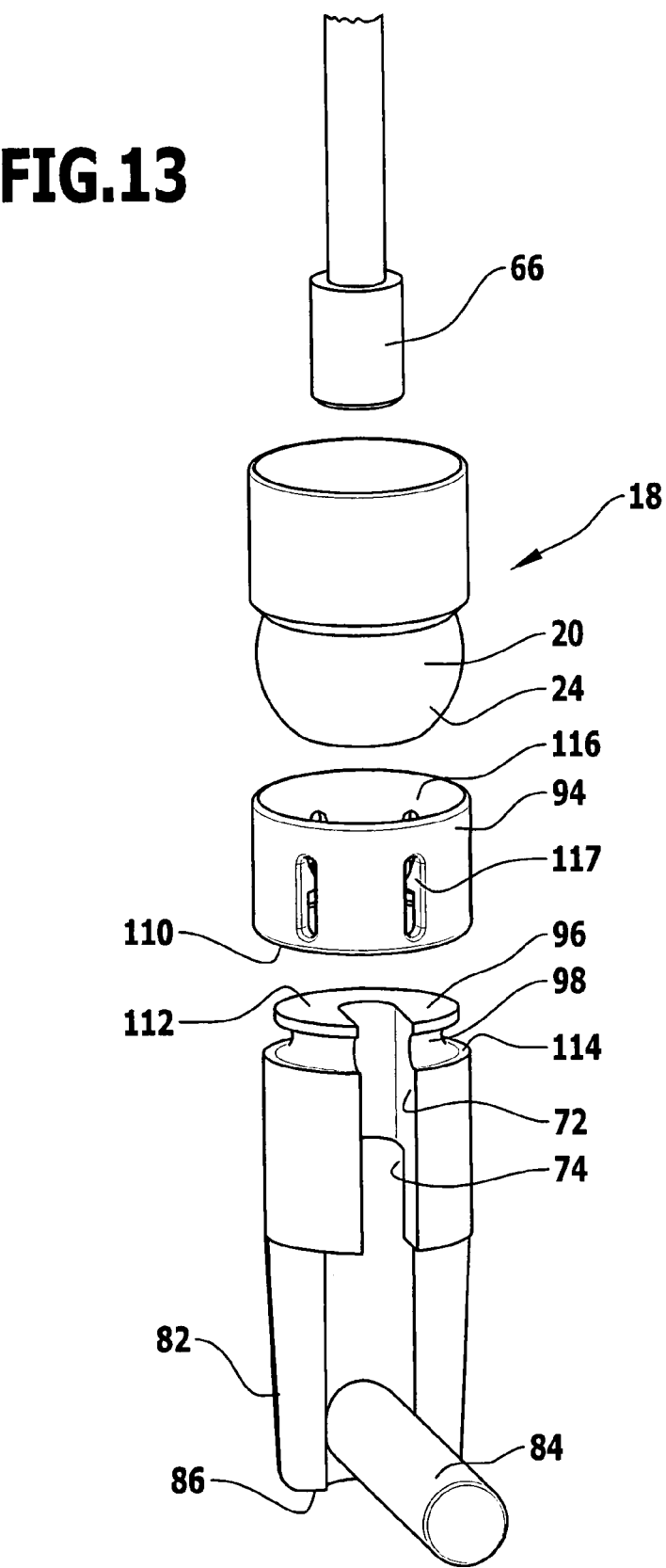
FIG. 13: shows an exploded illustration of the distal end of the holding arm with parts separated from one another.

In order to transfer the holding arm 12 from the adjusting position, which is illustrated in FIG. 8, into the so-called operative position, in which the holding arm members 18 are tensioned against one another so as to be immovable, the tensioning member 162 need merely be turned about the longitudinal axis 168, namely in a direction such that the second stop 230 moves away from the movement limiting member 204 and the first stop 228 moves in the direction towards the movement limiting member 204. The toggle 198 can be turned only to such an extent until the first stop 288 abuts on the movement limiting member 204. In the operative position, the longitudinal axis 184 extends somewhat to the side next to the plane 226, which means that to reach the operative position the tensioning member must pass through a proximal dead center position, in which the longitudinal axis 184 is located in the plane 226 and in which a distance between the longitudinal axis 184 and the proximal end stop 42 is at a maximum. In the operative position, the holding arm members 18 are tensioned against one another in a clamped manner. On account of the tensile forces acting in the operative position, the tensioning member 162 is automatically blocked and cannot turn back into the adjusting position of its own accord. By turning the toggle 198 in the opposite direction, the holding arm 12 can be transferred out of the operative position into the adjusting position again.

In order to transfer the holding arm 12 into the cleaning position again, in which a distance 254 between individual holding arm members 18 can be up to 15 mm large, the movement limiting member 204 must be moved away, first of all, and the first coupling member 180 turned into its most distal position. In this case, the lever arm 200 of the toggle 198 points in a distal direction. The movement limiting member 204 can then be connected to the proximal tensioning part 48 again and be brought into engagement with the recess 222, whereby the tensioning member 62 is again secured on the proximal tensioning part 48 so as to be immovable.

If the cable line 36 is stretched somewhat during longer use of the holding arm 12, the holding arm member adapter 134 can be adjusted relative to the bearing member 118 by means of the adjusting device 158 in order to alter a distance between the proximal end stop 42 and the tensioning member 162, whereby, altogether, the distance 256 between the end stops 42 and 44 or rather a free length of the cable line 36 between the end stops 42 and 44 can be altered.

The movement limiting device 202 is, therefore, designed in such a manner that the holding arm 12 either can be brought only from the adjusting position into the operative position and vice versa or takes up only the cleaning position in a defined manner. In order to transfer the holding arm 12 from the adjusting position into the cleaning position and vice versa, the movement limiting member 204 and the tensioning member 162 can be brought out of engagement in the manner described above.

Furthermore, it should be mentioned, in addition, that the securing device 92 is designed in such a manner that the securing position and the release position can be taken up not only in the operative position but also in the adjusting position and also in the cleaning position.

The holding arm 12 is produced from one or several materials which can be sterilized by steam, preferably from an instrument steel.

The invention claimed is:

1. Surgical holding arm, comprising:
   a plurality of holding arm members coupled to one another,
   a tensioning device for tensioning the holding arm members against one another, the tensioning device comprising a tensioning element passing through the holding arm members, a tensioning member coupled to a proximal end of the tensioning element, and a proximal tensioning part, the tensioning member adapted to be rotated about an axis of rotation extending perpendicular to a longitudinal axis of the tensioning element, and
   a movement limiting device for limiting movement of the tensioning member relative to the proximal tensioning part, the movement limiting device comprising a least one stop for interacting with correspondingly designed stop surfaces on the tensioning member for defining at least one of an operative position, an adjusting position, and a cleaning position when in contact with the tensioning member,
   wherein:
      the tensioning member is eccentrically coupled with respect to the axis of rotation to the proximal end of the tensioning element,
      the tensioning device is designed in such a manner that the holding arm is adapted to be brought from said operative position, the holding arm members being tensioned against one another so as to be immovable in said operative position, into said adjusting position via rotation of the tensioning member of less than 360 degrees, the holding arm members being movable relative to one another in said adjusting position,
      the holding arm is adapted, in addition, to be brought into said cleaning position via the rotation of the tensioning member of less than 360 degrees, adjacent holding arm members being movable away from one another further in said cleaning position than in the adjusting position; and
      the movement limiting device is designed in such a manner that in a first limiting position the tensioning member is adapted to be brought from the operative position into the adjusting position and vice versa.

2. Surgical holding arm as defined in claim 1, wherein the tensioning device further comprises a proximal and a distal end stop and wherein a maximum distance between the distal and the proximal end stops is greater in the cleaning position than in the adjusting position.

3. Surgical holding arm as defined in claim 1, wherein the tensioning element is designed in the form of a cable line.

4. Surgical holding arm as defined in claim 2, wherein a free length of the tensioning element between the proximal and the distal end stops is variable with the tensioning device.

5. Surgical holding arm as defined in claim 1, wherein the tensioning device further comprises a distal tensioning part, wherein a distal end of the tensioning element is mounted and/or held on the distal tensioning part and the proximal end of the tensioning element is mounted and/or held on the proximal tensioning part.

6. Surgical holding arm as defined in claim 5, further comprising a securing device for securing the distal end of the tensioning element on the distal tensioning part in a securing position.

7. Surgical holding arm as defined in claim 6, wherein the securing device is adapted to be brought from the securing position into a release position, the distal end of the tensioning element being separable or releasable from the distal tensioning part in said release position.

8. Surgical holding arm as defined in claim 5, wherein the tensioning member is held on the proximal tensioning part so as to be movable.

9. Surgical holding arm as defined in claim 1, wherein the movement limiting device is designed in such a manner that in a second limiting position the tensioning member is adapted to be secured on the proximal tensioning part so as to be immovable or essentially immovable in the cleaning position.

10. Surgical holding arm as defined in claim 1, wherein the movement limiting device comprises at least one movement limiting member interacting with the tensioning member in at least one of the first limiting position and a second limiting position.

11. Surgical holding arm as defined in claim 10, wherein the at least one movement limiting member is in engagement with the tensioning member in a force and/or form locking manner in the cleaning position.

12. Surgical holding arm as defined in claim 10, wherein the movement limiting device comprises first and second stops interacting with the at least one movement limiting member and wherein the movement limiting member and one of the stops are in contact with one another in the adjusting position.

13. Surgical holding arm as defined in claim 10, wherein the tensioning member has a first recess, the movement limiting member engaging in said recess in the cleaning position.

14. Surgical holding arm as defined in claim 12, wherein the tensioning member has a second recess defining the first and second stops of the movement limiting device.

15. Surgical holding arm as defined in claim 10, wherein the at least one movement limiting member is designed in the form of a bolt adapted to be releasably connected to the proximal tensioning part.

16. Surgical holding arm as defined in claim 10, wherein the movement limiting member and the tensioning member are adapted to be brought out of engagement for transferring the holding arm from the adjusting position into the cleaning position and vice versa.

17. Surgical holding arm as defined in claim 8, further comprising an adjusting device for altering a distance of the proximal end stop and the tensioning member relative to one another.

18. Surgical holding arm as defined in claim 5, wherein the distal tensioning part and the proximal tensioning part each comprise at least one coupling element for connecting the holding arm to corresponding coupling elements of at least one of surgical holding devices, surgical instruments, surgical tools, and surgical equipment.

19. Surgical holding arm as defined in claim 1, wherein a holding arm member joint is formed at least between two adjacent holding arm members.

20. Surgical holding arm as defined in claim 19, wherein the holding arm member joint or the holding arm member joints are designed in the form of ball-and-socket joints or hinge joints.

21. Surgical holding device for holding and securing at least one of surgical instruments, surgical tools, and surgical equipment, comprising:
 at least one holding arm with a plurality of holding arm members coupled to one another,
 a tensioning device for tensioning the holding arm members against one another, the tensioning device comprising a tensioning element passing through the holding arm members, a tensioning member coupled to a proximal end of the tensioning element, and a proximal tensioning part, the tensioning member adapted to be rotated about an axis of rotation extending perpendicular to a longitudinal axis of the tensioning element, and
 a movement limiting device for limiting movement of the tensioning member relative to the proximal tensioning part, the movement limiting device comprising a least one stop for interacting with correspondingly designed stop surfaces on the tensioning member for defining at least one of an operative position, an adjusting position, and a cleaning position when in contact with the tensioning member,
 wherein:
  the tensioning member is eccentrically coupled with respect to the axis of rotation to the proximal end of the tensioning element,
  the tensioning device is designed in such a manner that the holding arm is adapted to be brought from said operative position, the holding arm members being tensioned against one another so as to be immovable in said operative position, into said adjusting position via rotation of the tensioning member of less than 360 degrees, the holding arm members being moveable relative to one another in said adjusting position,
  the holding arm is, in addition, adapted to be brought into said cleaning position via rotation of the tensioning member of less than 360 degrees, adjacent holding arm members being movable away from one another further in said cleaning position than in the adjusting position; and
  the movement limiting device is designed in such a manner that in a first limiting position the tensioning member is adapted to be brought from the operative position into the adjusting position and vice versa.

22. Surgical holding device as defined in claim 21, wherein the tensioning device comprises a proximal and a distal end stop and wherein a maximum distance between the distal and the proximal end stops is greater in the cleaning position than in the adjusting position.

23. Surgical holding arm as defined in claim 1, wherein the tensioning member is adapted to be fixed in the cleaning position.

24. Surgical holding device as defined in claim 21, wherein the tensioning member is adapted to be fixed in the cleaning position.

* * * * *